United States Patent [19]

Cambio, Jr.

[11] 4,201,208
[45] May 6, 1980

[54] STERILE CONNECTING DEVICE

[75] Inventor: Orlando D. Cambio, Jr., Bristol, Wis.

[73] Assignee: Abbott Laboratories, North Chicago, Ill.

[21] Appl. No.: 855,647

[22] Filed: Nov. 30, 1977

[51] Int. Cl.² ............................................. A61M 5/00
[52] U.S. Cl. ................................ 128/214.2; 128/247; 128/272.3; 141/329; 222/83; 285/3
[58] Field of Search ............... 128/247, 214 R, 214.2, 128/214.4, 272, 272.1, 272.3, 214 C, 214 D, DIG. 5; 215/247, 249, 250, 251, 258, DIG. 3; 206/222; 222/81, 82, 83, 83.5; 141/329, 330, 19; 285/3, 4

[56] References Cited

U.S. PATENT DOCUMENTS

| | | | |
|---|---|---|---|
| 2,689,564 | 9/1954 | Adams et al. | 128/214 R |
| 2,847,995 | 8/1958 | Adams | 128/214 R |
| 3,336,924 | 8/1967 | Sarnoff et al. | 128/272.3 |
| 3,606,077 | 9/1971 | Faust | 220/66 |
| 3,685,795 | 8/1972 | Caster | 128/214.2 X |
| 3,915,212 | 10/1975 | Bujan et al. | 128/214 D X |
| 3,945,528 | 3/1976 | Mowrey, Jr. | 215/250 X |

FOREIGN PATENT DOCUMENTS 2402310   7/1974   Fed. Rep. of Germany ........ 128/272.3

*Primary Examiner*—J. Reed Fisher
*Attorney, Agent, or Firm*—Robert L. Niblack; Neil E. Hamilton

[57] ABSTRACT

A connecting device which will provide a sterile connection between a container for sterile solutions and tubing for delivery of the fluid. A piercing pin is provided having a pointed end with a pin sheath surrounding the pointed end and in contact with it. The sheath surrounds the hub member of the pin and upon contact with a pierceable diaphragm, the sheath breaks away from the pointed end of the pin allowing it to become exposed with the sheath then surrounding in a uniform manner the hub member of the pin. To facilitate the uniform movement of the sheath around the hub, a shoulder section is provided in the sheath for contact with an accommodating shoulder portion of the container closure having the diaphragm. In a preferred manner, two pierceable diaphragms are provided in the closure system on the container. The first provides the initial contact and the breaking of the sheath away from the piercing pin; the second provides sterile contact between the now exposed point of the piercing pin for sterile penetration into the container.

10 Claims, 12 Drawing Figures

STERILE CONNECTING DEVICE

BACKGROUND OF THE INVENTION

This invention relates to a sterile connecting device to provide fluid communication with the sterile contents of a container. More particularly, this invention relates to a piercing pin device having a sheath which will break away from the piercing pin upon contact with and penetration through a pierceable diaphragm forming a part of a container closure.

Piercing members with sheaths of the type concerned with in this invention are disclosed in U.S. Pat. Nos. 2,689,564 and 2,847,995. However, the sheaths surrounding the piercing needles in these patents have the disadvantage of not being fully and uniformly collapsible of slidable along the hub of the needle so as to afford accurate and sterile penetration. Neither does the prior art illustrate the utilization of a slidable or collapsible sheath over the hub of a piercing pin during penetration of a closure diaphragm in conjunction with a closure system which has two spaced-apart diaphragm members to reduce the risk of any contamination during connection with the piercing pin. In U.S. Pat. No. 3,606,077, a guide for a piercing pin is shown in conjunction with a pierceable diaphragm. However, this particular patent is not concerned with a guide for a piercing pin having a break-away and uniformly removable sheath as is disclosed herein. There is not presently available a sterile connecting system which will substantially reduce the risks of contamination frequently attributed to poor technique by the fluid administrator.

It is an advantage of the present invention to afford a sterile connecting device for use in conjunction with a sterile container. Other advantages are a sterile connecting pin having a sheath which will break away from the piercing pin in a substantially symmetrical manner and will uniformly surround the hub of the piercing pin; a piercing member with a break-away sheath which is especially suited for piercing through a double diaphragm structure in a container closure; and a break-away sheath for a piercing pin which will be retained in the container closure.

SUMMARY OF THE INVENTION

The foregoing advantages are accomplished and the shortcomings of the prior art are overcome by the present connecting device which includes a piercing pin having a pointed end with a hub member extending oppositely from the pointed end. A pin sheath surrounds the pointed end of the piercing pin and is in direct contact with it. The sheath is attached to the hub member and includes a shoulder member intermediate between that portion in contact with the pointed end and that attached to the hub portion. Upon contact with a container diaphragm, the portion of the pin sheath surrounding the pointed end will break away laterally and in a substantially symmetrical manner. Upon subsequent contact with the shoulder member with a supporting shoulder section of the container closure, the sheath will uniformly surround the hub of the piercing pin. In one embodiment, the hub member has a longitudinal axis and the sheath is constructed and arranged to slide thereover as the piercing pin penetrates through the diaphragm and into the container. In another embodiment, the sheath is defined by a bellows portion extending between the shoulder section and its attachment to the hub member so that it will uniformly fold over the hub. In addition, connection means can be provided between the sheath and the hub member to retain it on the hub and the inside of the sheath can be formed with internal serrations to facilitate holding or locking of the pin sheath onto the pin. The piercing pin device of this invention is especially adapted for piercing through a double diaphragm container closure member and can be provided with a combined break-away and retaining means for captive engagement with a closure member.

DESCRIPTION OF THE DRAWING

A better understanding of the fluid transfer system of this invention will be accomplished by reference to the drawing wherein.

DESCRIPTION OF ONE EMBODIMENT

Figure 1:
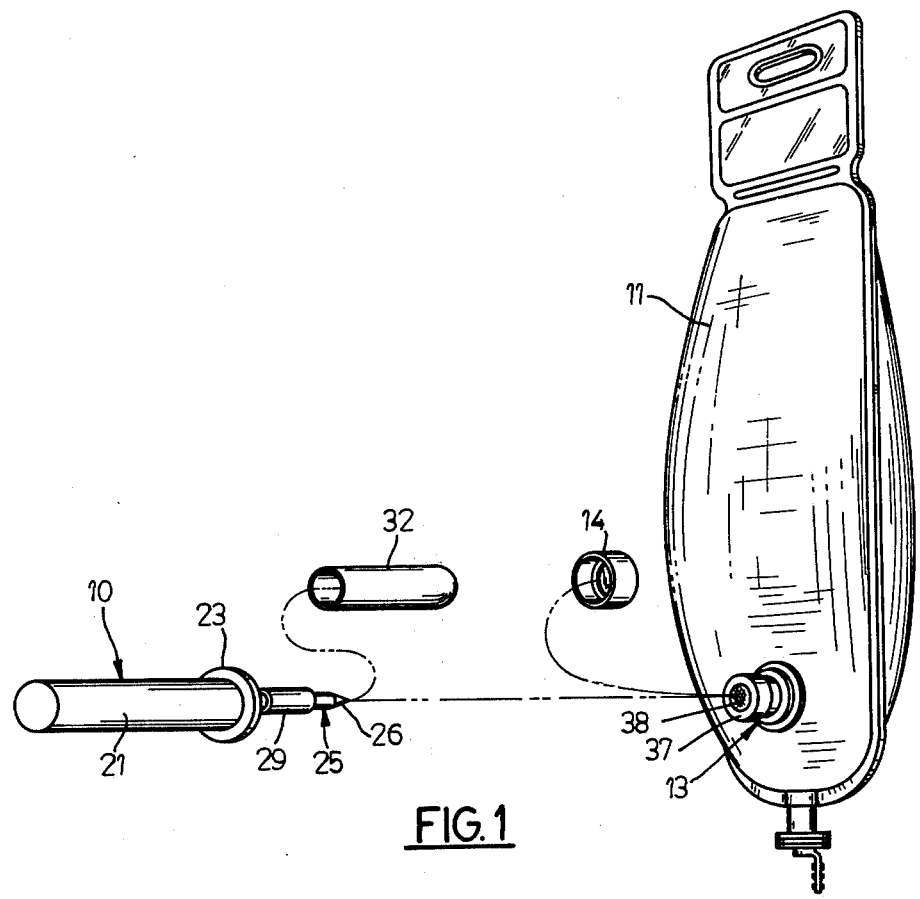
FIG. 1 is a perspective view of a flexible intravenous solution bag with the piercing pin member of this invention shown in an orientated position with respect to the pierceable closure on the container.

Proceeding to a detailed description of the present invention, the connecting device 10 is shown in FIG. 1 in conjunction with a resinous plastic, flexible I.V. solution bag 11 of the type described in U.S. Pat. No. 3,915,212 entitled "Flexible Medicinal Fluid Container Having a Combined Fill and Administration Port and Reinforced Hanger" and is commonly assigned. The container 11 has a container closure 13 with a removable cap 14. Connecting device 10 includes a hollow piercing pin 15 having a pointed end 16 and a hub member 18. A length of flexible tubing 21 which will be further connected to the usual apparatus for intravenous administration is in fluid-tight communication with piercing pin 15. The usual finger grip 23 is also provided as well as removable pin cover 32.

Figure 2:
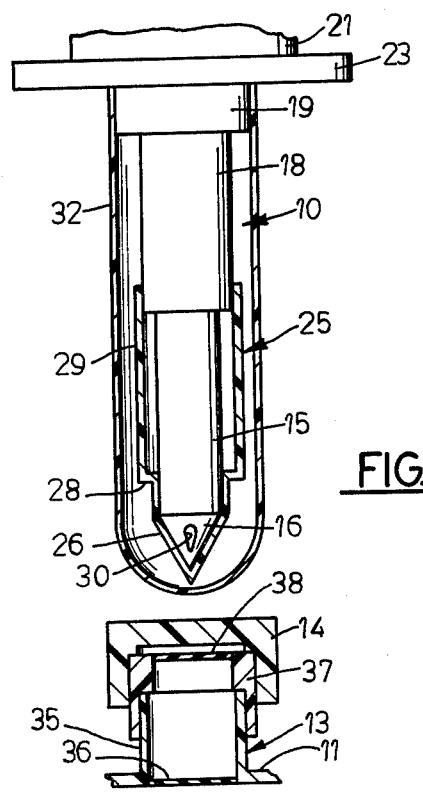
FIG. 2 is an enlarged view in side elevation of the piercing pin connecting device shown in FIG. 1 as well as a view in vertical section of the container closure system, with certain parts of the piercing pin device shown in vertical section.

As best seen in FIG. 2, a slidable sheath 25 is disposed partially around hub member 18 and is in direct contact with the pointed end 16 of the piercing member thus affording a pointed end 26 for the sheath. A shoulder 28 is disposed between the tubular wall 29 of the sheath and the pointed end 26. The usual opening 30 is disposed through the tip 16 of the hollow piercing member. Cap 32 is movably retained over the piercing pin and the sheath by means of a stepped connecting portion 19. Also seen in FIG. 2 is the double diaphragm closure for container 11 wherein a diaphragm 38 is carried by a diaphragm housing 37 covered by the removable cap 14 and remote from container 11. Diaphragm housing 37 is sealed to a tubular container port 35 with diaphragm 36 sealed at the inside of the tubular port 35 and proximal to the container.

Figure 6:
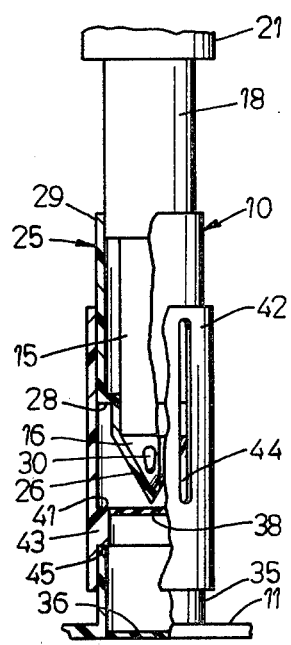
FIG. 6 is a view in side elevation with parts broken away illustrating an alternative embodiment.

In FIG. 6, a tubular guide 42 is shown with a reduced diameter section 43 providing an appropriate shoulder 45 for resting on container port 35. Another shoulder section 41 is also disposed inside the tubular guide 42 and the remotely disposed diaphragm 38 is sealed across at this particular point.

Figure 7:
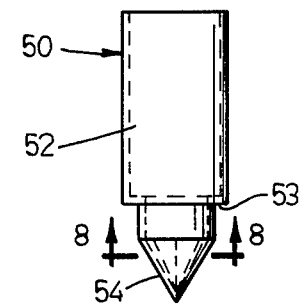
FIG. 7 is a view in side elevation of a sheath member for utilization with the piercing pin of this invention showing another embodiment.
Figure 8:
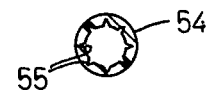
FIG. 8 is a view in horizontal section taken through line 8—8 of FIG. 7.

In FIG. 7, a modification of a pin sheath is shown at 50 having a tubular wall 52 with a shoulder 53 disosed between wall 52 and the pointed end 54 of the sheath 50. As seen in FIG. 8, the pointed end 54 has internal serrations 55 to aid in the breaking of the sheath which will be further explained during the Operation.

Figure 9:
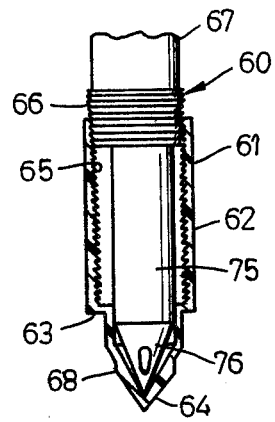
FIG. 9 is a view in side elevation with portions shown in vertical section illustrating still another embodiment.
Figure 10:
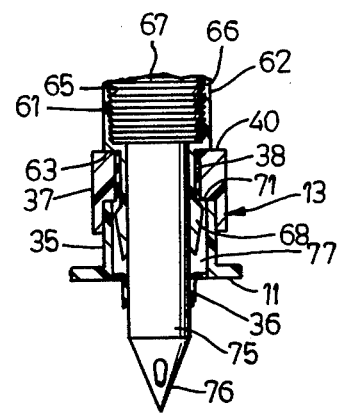
FIG. 10 is a view similar to FIG. 9 showing the embodiment of FIG. 9 penetrating through a double diaphragm closure system, with the closure shown in vertical section.

FIG. 9 illustrates an alternative embodiment of a connecting device 60 wherein the pin sheath 61 having a tubular wall 62 as well as a shoulder 63 and a pointed end 64 includes ribs 65 on the sheath as well as complementary engaging ribs 66 on hub 67. With ribs 65 and 66 on both the sheath and the hub, respectively, a connecting means is afforded between the sheath and the hub during and after penetration by the pointed end 76 of the piercing pin as it penetrates the diaphragm 38 and 36 as shown in FIG. 10. It will also be noted in FIG. 9 that the pointed end of the sheath 64 is enlarged such as shown at 68. This affords a retaining means which will engage the interior shoulder 71 of the container closure 13 upon any attempted removal of the piercing pin 75 from the container closure. Further, for more effective breaking of sheath point 64, it is formed at a wider angle than point 76.

Figure 11:
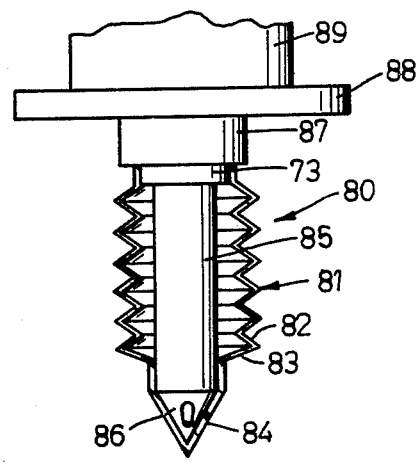
FIG. 11 is a view in side elevation showing still another embodiment with parts shown in vertical section.

In FIG. 11, a further embodiment of the connecting device 80 is shown with a pin sheath 81 having a tubular wall 82 which is in the form of a bellows. A shoulder 83 is disposed, as in the other embodiments, between the pointed end 84 and the tubular wall 82. A hollow piercing pin 85 is disposed inside the sheath 81 and has a pointed end 86 as well as a hub portion 73 for connection with wall 82. A stepped connecting portion 87 secures tubing 89 with a finger grip portion 88 therebetween.

Figure 12:
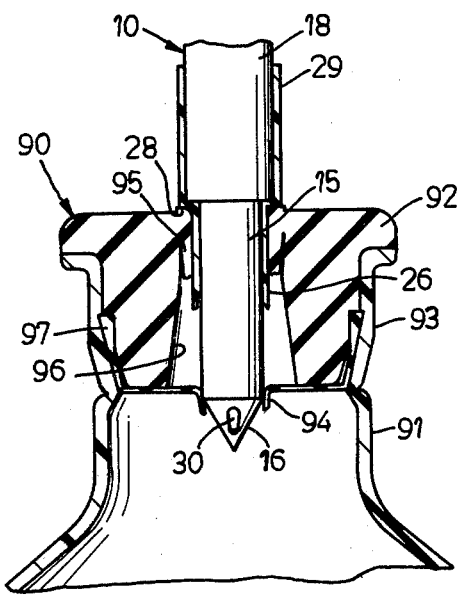
FIG. 12 is a view in side elevation showing the piercing pin connecting device of this invention operable with a particular closure system on a bottle and with portions shown in vertical section.

FIG. 12 illustrates a different closure system 90 in conjunction with a container 91 of the bottle or semi-rigid plastic type as described in U.S. Pat. No. 4,013,187 entitled "Hanger Construction for Semirigid Plastic Container," commonly assigned. This closure system is operable with the connecting devices 10, 60 or 80 as previously described, and includes a stopper closure 92 disposed on container neck 93. Proximal diaphragm 94 is sealed across the container neck and seals the closure 92 from the contents of container 91. A remote diaphragm 95 is disposed near the outer edge of stopper closure 92. A tubular passageway 96 is provided between the two diaphragms.

OPERATION

Figure 3:
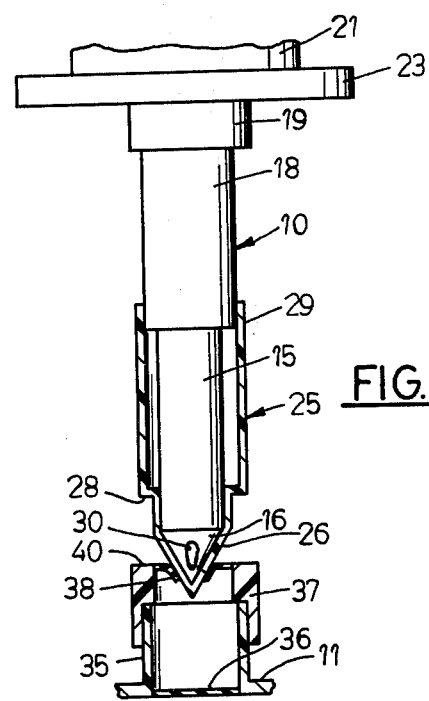
FIG. 3 is a view similar to FIG. 2 except showing the connecting device in the first stage of penetration through a diaphragm in a container closure.
Figure 4:
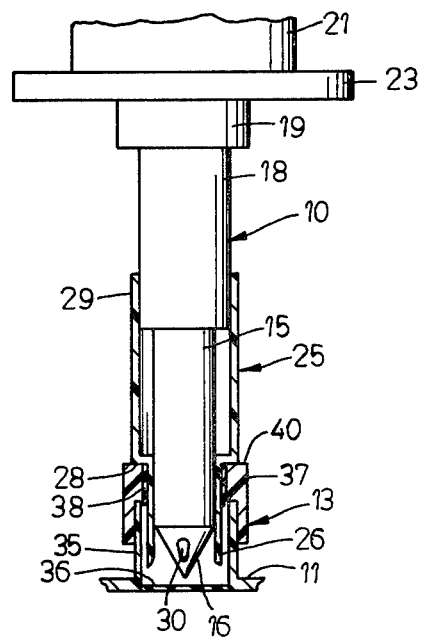
FIG. 4 is a view similar to FIG. 3 showing a subsequent stage of movement of the piercing pin connecting device through the container closure.
Figure 5:
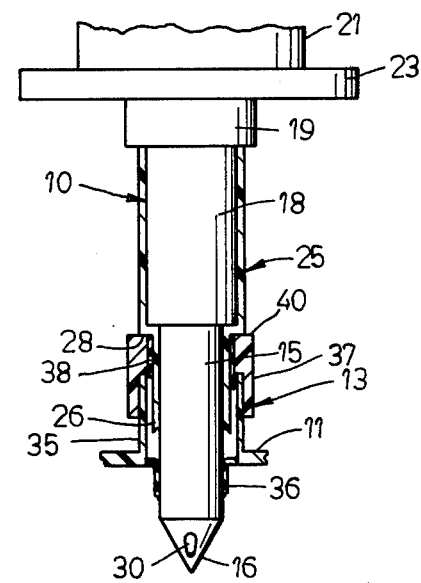
FIG. 5 is a view similar to FIG. 3 showing the piercing pin penetrating both diaphragms and in fluid communication inside the container.

A better understanding of the advantages of the connecting devices 10, 60 and 80, as well as pin sheath 50 will be had by a description of their operation. Referring to connecting device 10, it will be packaged with pin cover 32 frictionally secured to the stepped connecting portion 19. Connecting unit 10 will be sterilized as will container 11 and the container closure 13 in the normal manner. When it is desired to utilize the connecting device 10 so as to afford fluid communication with the inside of closure 11, pin cover 32 will be removed as will closure cap 14, as shown in FIG. 1. The pointed end 26 of sheath 25 as well as the pointed end 16 of piercing pin 15 will then contact and pierce through the remote diaphragm 38 of closure 13 as shown in FIG. 3. Sheath 25 will ride with pin until shoulder 28 contacts the upper shoulder surface 40 of diaphragm housing 37. When this occurs, the pin 15 will continue to move but the movement of sheath 25 will stop, thus causing that portion 26 of the pointed end of the sheath to break away laterally and expose the pointed end of pin 16 as best shown in FIG. 4. There now exists a completely sterile piercing point 16 for pin 15 which will be positioned in a sterile chamber in tubular container port 35 previously sealed by remote diaphragm 38 and proximal diaphragm 36. At this stage, however, the diaphragm 38 will be broken open and will be disposed between broken sheath pointed end 26 and diaphragm housing 37. Further movement of the pin 15 with the shoulder 28 of sheath 25 resting on the shoulder surface 40 of the diaphragm housing will cause the tubular wall 29 of sheath 25 to ride over and be accommodated in a uniform and surrounding manner along the longitudinal axis of hub member 18. In its final placement piercing pin 15 will be positioned as shown in FIG. 5. It should be realized that not only is there provided a sterile piercing point which reduces any likelihood of contact with any nonsterile surface before contacting the sterile liquid, but any sterile air which might be trapped between the tubular wall 29 of the sheath and the piercing pin 15 will be compressed and seek its way out from between the sheath and the hub 18 or from the pointed end portion of the pin during insertion of the pin through the double diaphragms. This is an added advantage in that it is positive sterile air which is being expelled and not surrounding air which might be drawn into a system which might be under a vacuum.

If it is desired to air in the alignment of connecting devices 10, 60 and 80 when they are inserted through the diaphragms 38 and 36, a tubular guide 42, as best shown in FIG. 6, can be provided. It will be appreciated that when the tubular guide 42 is utilized in conjunction with the piercing pins such as 15 and sheath 25, there would be air compressed inside guide 42. Accordingly, a tube vent 44 is provided so that the air can escape. In all other respects, the operation of the unit 10, or units 60 and 80, in conjunction with the container port 35 and guide 42 shown in FIG. 6 will be as previously described.

In order to aid the breaking away of the sheath points such as shown at 54 in FIG. 7, serrations 55 can be internally provided. This affords two advantages in that it aids in the uniform tearing away of the sheath as well as reduces contact between the pointed end of the pin 15 and the pointed end of the sheath 54. If it is desired to have the piercing pin retained in the closure, then the embodiment 60 shown in FIGS. 9 and 10 can be utilized. In such instance, piercing pin 60 will be utilized as previously described for unit 10 except that after piercing through the double diaphragms 38 and 36, the enlarged section 68 previously surrounding the pointed end 76 of piercing pin 75 will be retained in the tubular passage 77 formed between diaphragms 36 and 38. Any attempt to remove pin 75 will cause the enlarged portion 68 of the sheath to contact internal shoulder 71 of diaphragm housing 37. In turn, sheath 61 will be retained on hub 67 by the interengagement of the annular ribs 65 on the sheath and 66 on the hub. It will be further noted in conjunction with FIG. 9 that the pointed portion 64 of the sheath 61 can be formed at a wider angle than the piercing point 76 on the pin to afford a better and uniform breaking action.

Connecting device 80 as shown in FIG. 11 will operate essentially the same as connecting unit 10 except that instead of the tubular wall 29 sliding over a hub 18 as in unit 10, a bellows effect is afforded by the pleated tubular wall 82. This embodiment offers the advantage in that extending hub portion such as 18 does not have to be provided as the tubular wall 82 of sheath 81 will collapse upon itself over piercing pin 85.

Piercing unit 10 is shown in FIG. 12 in operation with a stopper closure 92 which will be considerably larger than closure 13 for bag 11, as the closure is disposed on a large-type container 91 such as a semirigid plastic bottle. Piercing pin unit 10 will readily operate in connection with such a closure system in that the piercing pin 15 is well designed to reach through the passageway 96 and pierce through both diaphragms 95 and 94 so that the opening 30 of the piercing pin is in full communication with the contents of container 91 before hub 18 contacts the upper surface of stopper closure 92. It will be noted that the particular closure 90 offers the added advantage in providing the proximal diaphragm 94 completely across the inner surface of stopper 92 thereby serving as a barrier between the contents of container 91 and the closure. Obviously, connecting units 60 and 80 are also operable with closure 92.

An important aspect to cause the sheath pointed ends 26, 54, 64 and 84 to break in a lateral and uniform manner from the respective piercing points of the pins is to have the resulting internal configuration of the sheath point uniformly walled and such that it is an approximate mating fit with the pin point. As a result, the forces which are applied during the connection process will be distributed over the entire pin point surface and its mating sheath and not just the point tip, as is the case when puncturing a flat diaphragm. Unless the sheath is made of an extremely thin, fragile material, the connection would be difficult because excessive force would be required to penetrate the sheath.

There are at least two negative factors connected with making the sheath tip from an extremely thin, fragile material:
(a) The sheath would most likely puncture prematurely such as before the shoulders made contact;
(b) If the external surface of the sheath was contaminated, the pin would be more likely to become contaminated because of the proximity of the external surface to the pin surface.

One way to avoid this problem is to make the pin point angle smaller than the external sheath point angle, as in FIG. 9, and to make the sheath wall suitably thick with frangible webs on the outside surface. As the axial connecting force is translated into a more radial direction of the pin point, circumferential stresses are created within the sheath tip. The easiest web to break would be one perpendicular to these stresses. A series of these webs permits the sectors which result after web breakage to swing away from the advancing pin. If the frangible web were located around the circumference of the sheath tip, greater force would be required to break it and it would result in a loose piece of plastic floating in the solution which is considered objectionable in I.V. therapy. Further in conjunction with the sliding of tubular wall 29 of sheath 25 over hub 18, wall 29 should be fabricated such that a slight interference fit exists initially and the sheath capable of expanding radially as the mating pin and sheath tapers are brought together during penetration. The tapers are a result of the slight draft angles which are required by the injection molding process.

Pins 15, 75 and 85 can be fabricated from plastic materials such as acrylonitrile-butadiene-styrene or other hard, strong materials. Sheaths 25, 50, 61 and 81 are fabricated from polyethylene or similar soft and fragile material. Accordingly, the connecting devices are completely disposable as they can be fabricated in a very economic manner. The diaphragms such as 36 and 38 can be formed from polyvinyl chloride whereas diaphragms 94 and 95 are composed of rubber or polypropylene. However, other penetrable, fragile, compatible, low extractable, thermoplastic or elastomeric materials could be used which are readily secured to either flexible bag 11, the diaphragm housing 37 or rubber closure 92 in the usual manner such as heat sealing or friction or mechanical fit in the case of closure 92.

It will thus be seen that through the present invention there is provided a sterile connecting system for communicating with the sterile contents of a flexible container which substantially reduces the risk of contamination prior to communicating with the inside of the container. The piercing pin connecting device of this invention affords an easy to use and unique break-away feature for a sheath such that the sheath is not prematurely pierced, does not introduce substantial amounts of particulate matter or interfere during pin piercing of a diaphragm, especially where the pin is utilized in conjunction with the penetration of two spaced apart closure diaphragm members. A guide member can be provided if necessary where the closure port is relatively small and various techniques such as serrating the inside of the sheath and the design of different angles for the sheath and the pin points can be easily utilized in conjunction with the piercing pin units. In addition, all of the units illustrated herein are completely disposable and can be molded without the need of special materials or special molding or sealing techniques.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:
1. A fluid transfer system which substantially reduces contamination comprising:
a container for sterile fluids;
a closure secured to said container including a hollow tubular passageway sealed by means of a first pierceable diaphragm and a second pierceable dia- phragm, said first diaphragm positioned remote from said container and said second diaphragm positioned proximal thereto to provide a sterile chamber therebetween and said closure including a shoulder section disposed outwardly from said first diaphragm;

a hollow piercing pin having a pointed end and adapted to be inserted into said tubular passageway and penetrate said diaphragms;

a hub member extending from said piercing pin opposite said pointed end;

a sheath surrounding the pointed end of said piercing pin and in direct contact with the pointed end thereof, said sheath attached to said hub member and defining a shoulder member intermediate a portion contacting said pointed end and a portion attached to said hub member, said sheath surrounding said piercing pin including said pointed end and said hub member in a uniform manner;

so that upon contact with said first diaphragm said portion of said pin sheath surrounding the pointed end of said piercing pin will pierce through said first diaphragm and upon further movement said sheath shoulder member will contact said shoulder section of said container closure, and said pin sheath surrounding the pointed end of said piercing pin will break away laterally exposing the pointed end of said piercing pin and said sheath will uniformly surround the hub of said piercing pin as said pointed end of said piercing pin pierces through said second diaphragm.

2. The connecting device as defined in claim 1 wherein the portion of said pin sheath surrounding the pointed end of the piercing pin includes a retaining means carried by said sheath.

3. The connecting device as defined in claim 1 wherein said hub member has a longitudinal axis and said sheath is constructed and arranged to slide thereover as said piercing pin penetrates into said container.

4. The connecting device as defined in claim 3 wherein said hub and said sheath surrounding said hub are temporarily retained by connecting means.

5. The connecting device as defined in claim 4 wherein said connecting means are defined by interengaging rib members.

6. The connecting device as defined in claim 1 wherein said sheath is defined by a bellows portion extending between said shoulder member and the attachment to said hub member so that said sheath will uniformly fold over said hub member.

7. The connecting device as defined in claim 1 wherein the pin sheath surrounding the pointed end of the piercing pin includes internal serrations to facilitate breaking of the pin sheath.

8. The connecting device as defined in claim 1 wherein the portion of said pin sheath surrounding the pointed end of the piercing pin includes a retaining means carried by said sheath and said closure further including an additional shoulder section positioned inwardly from said first diaphragm for interengagement with said sheath retaining means.

9. The connecting device as defined in claim 1 wherein the pin sheath surrounding said pointed end of said piercing pin has a pointed end with the point formed at a wider angle than the pin point.

10. The connecting device as defined in claim 1 further including a tubular guide member operatively associated with said closure tubular passageway and adapted to receive said piercing pin.

* * * * *